US 6,684,685 B2

(12) United States Patent
Gupta et al.

(10) Patent No.: US 6,684,685 B2
(45) Date of Patent: Feb. 3, 2004

(54) LIQUID EXTRUSION POROSIMETER AND METHOD

(75) Inventors: Krishna M. Gupta, Ithaca, NY (US); Akshaya Jena, Ithaca, NY (US)

(73) Assignee: Porous Materials, Inc., Ithaca, NY (US)

( * ) Notice: Subject to any disclaimer, the term of this patent is extended or adjusted under 35 U.S.C. 154(b) by 0 days.

(21) Appl. No.: 10/177,434

(22) Filed: Jun. 21, 2002

(65) Prior Publication Data

US 2003/0233865 A1 Dec. 25, 2003

(51) Int. Cl.$^7$ ............................................. G01N 15/08
(52) U.S. Cl. ............................................................. 73/38
(58) Field of Search .............................................. 73/38

(56) References Cited

U.S. PATENT DOCUMENTS

| 2,465,948 A | * | 3/1949 | Welge | 73/38 |
| 2,534,737 A | * | 12/1950 | Rose | 73/38 |
| 2,612,036 A | * | 9/1952 | Angona | 73/38 |
| 2,706,904 A | * | 4/1955 | Hertel | 73/38 |
| 2,755,660 A | * | 7/1956 | Kammermeyer et al. | 73/38 |
| 4,203,317 A | * | 5/1980 | Gupta | 73/38 |
| 4,660,412 A | | 4/1987 | Gupta | 73/38 |

FOREIGN PATENT DOCUMENTS

| RU | 229002 | * | 2/1969 | 73/38 |
| RU | 853492 | * | 8/1981 | 73/38 |
| RU | 1118900 | * | 10/1984 | 73/38 |
| RU | 1130772 | * | 12/1984 | 73/38 |
| RU | 1807341 | * | 4/1993 | 73/38 |

OTHER PUBLICATIONS

Thelen, E. "Soil Permeability Tester", Franklin Institute Laboratories Notes: Franklin Inst. Journal, vol. 253, Apr. 1952, pp. 340–341.*

* cited by examiner

Primary Examiner—Daniel S. Larkin
(74) Attorney, Agent, or Firm—Brown & Michaels, PC

(57) ABSTRACT

A porosimeter evaluates the porosity characteristics (specifically, pore volume, pore distribution and liquid permeability) of a porous sample of material. The porosimeter includes a fluid reservoir located below the sample, and a penetrometer comprising a vessel which catches any fluid displaced from the reservoir of fluid, wherein a level of fluid rises in the penetrometer when additional fluid enters the penetrometer. The sample is preferably wetted, with the same type of fluid which is in the reservoir, prior to placing the sample on the porosimeter. The porosimeter preferably also includes a membrane located between the sample and the reservoir of fluid. The membrane has pores with a size smaller than any of the sample pores. Pore volume of the sample is determined by measuring the change in fluid level in the penetrometer after pressure, which is above the bubble point pressure of the sample but below the bubble point pressure of the membrane, is applied to the sample. Permeability is measured by measuring rate of flow while the liquid level is above the sample.

23 Claims, 3 Drawing Sheets

PRIOR ART

LIQUID EXTRUSION POROSIMETER AND METHOD

BACKGROUND OF THE INVENTION

1. Field of the Invention

The invention pertains to the field of porosimetery, or the measurement of the porosity of substances. More particularly, the invention pertains to a liquid extrusion method and apparatus for determining the porosity characteristics of a sample.

2. Description of Related Art

The prior art measures the pore volume of a sample using a weight and balance method. Specifically, as shown in FIG. 1, a sample (1) is wetted by water and then placed above a membrane (2). A reservoir of fluid (3) is located below the membrane (2). This fluid is the same type of fluid which is used to wet the sample (1). A vacuum is used to draw the liquid through the sample.

In vacuum systems, pressure cannot be controlled accurately or maintained at a constant value. The low pressure causes loss of liquid from pores due to evaporation.

The prior art uses water as the wetting fluid. Water has high air diffusivity, which increases the air bubbles in a sample, and potentially yields inaccurate results by increasing the volume of the displaced liquid. The viscosity of water is low, which also leads to bubble formation.

This equation below used for computing pore diameter (D) from results of porosimetry shows that accuracy of measurement is determined by surface tension, $\gamma$, and contact angle, $\theta$, of the wetting liquid. For water $\gamma$ is large and changes easily due to contamination and $\theta$ is also large and varies appreciably depending upon the nature of the sample. These uncertainties contribute to error.

$$D = 4\gamma \cos \theta / P$$

The sample (1) has larger pores (4) than the pores (5) of the membrane (2). Vacuum (13) is applied, until liquid is drawn out of the pores (4) in the sample, and into the reservoir of fluid (3). The displaced fluid (7) flows over the top of the reservoir container (8) and is caught in a receptacle (9). The receptacle (9) is on a balance (10), which weighs the amount of the displaced fluid (7). This weight change is used in combination with calculations known in the art to determine the volume of the pores (4) in the sample (1). A counterweight (11) on the balance (10) is used to determine the weight change due to the displaced fluid (7).

SUMMARY OF THE INVENTION

A porosimeter evaluates the porosity characteristics of a porous sample of material. The sample is preferably wetted, with the same type of fluid which is in the reservoir, prior to placing the sample on the porosimeter, or the fluid can be poured over the sample in the chamber and pressure applied to force the fluid into the pores of the sample.

The porosimeter of the present invention comprises a source of pressure connected to a pressurizable chamber for holding the sample, and a reservoir of fluid located below the sample, to which is connected a penetrometer comprising a tube into which fluid displaced from the reservoir of fluid can flow. Thus, the level of fluid will rise in the penetrometer when additional fluid enters the reservoir, and by measuring the level of fluid in the penetrometer the volume of fluid entering the reservoir can be measured.

The sample is supported by a membrane located between the sample and the reservoir of fluid. The membrane has a plurality of pores with a size smaller than any of the sample pores, so that the bubble point pore diameter of the membrane is smaller than the smallest pore of interest in the sample.

The pore volume of the wetted sample is determined by applying a pressure which is above the bubble point pressure of the sample, but below the bubble point pressure of the membrane, and measuring the change in fluid level in the penetrometer.

Preferably, a fluorocarbon or silicone liquid is used as the fluid in the porosimeter. Fluorocarbon and silicone liquids have low surface tension and the contact angle is zero for many materials. The low surface tension enables smaller pores to be measurable. Unchanging surface tension gives more accurate data. Zero constant contact angle gives more accurate and less uncertain results.

The same apparatus can be used to measure permeability of the sample by measuring flow versus time when pressure is applied to the sample.

DETAILED DESCRIPTION OF THE INVENTION

Figure 1:
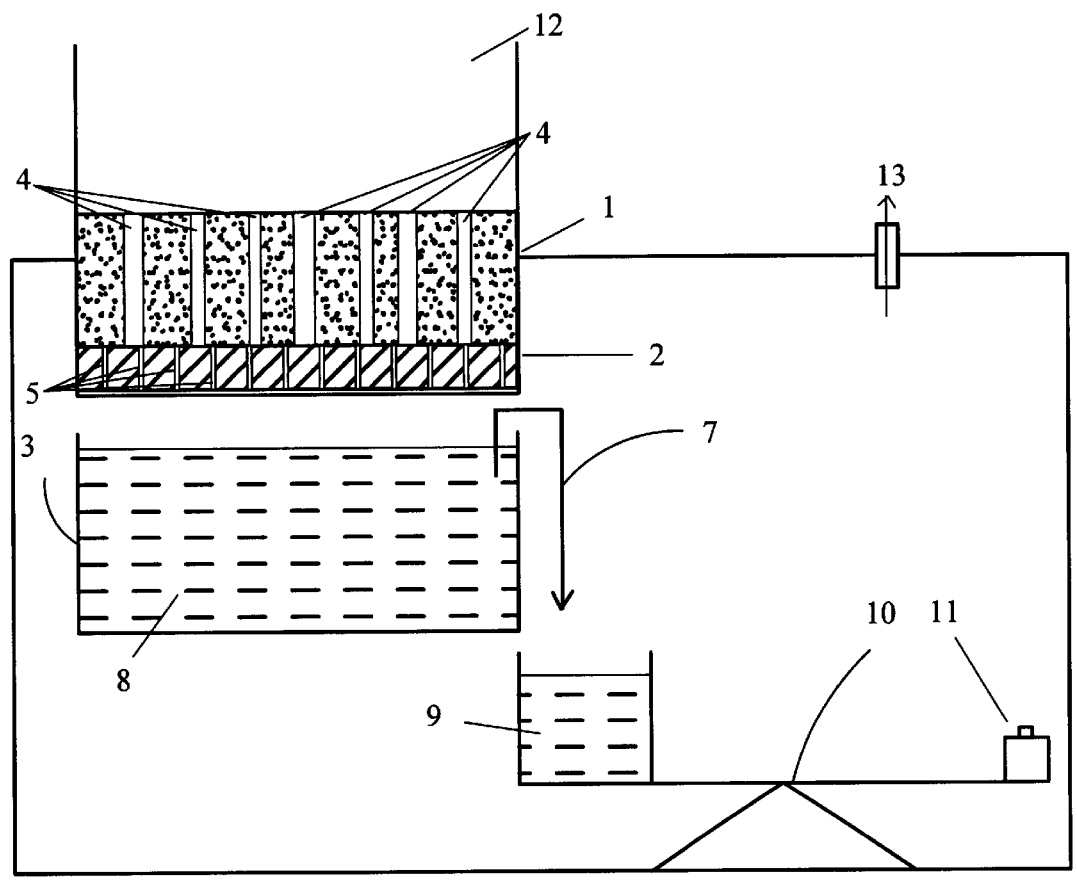
FIG. 1 shows a device for measuring pore volume as known in the prior art.
Figure 2:
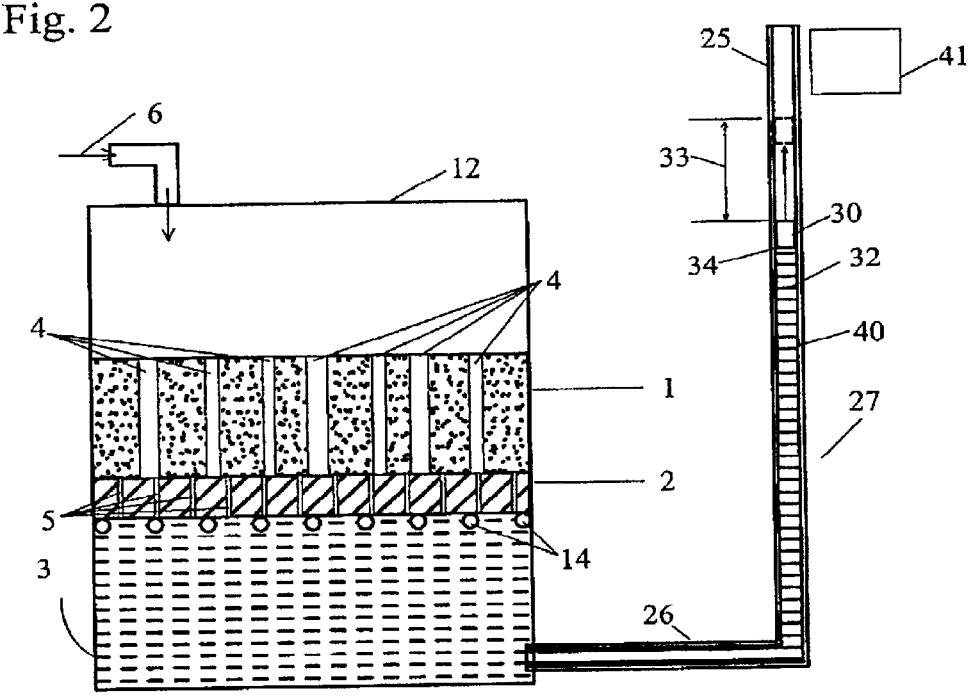
FIG. 2 shows a device for measuring pore volume and/or permeability in an embodiment of the present invention.

An example of a porosimeter of the present invention is shown in FIG. 2. A sample (1) of a material whose porosity characteristics are to be determined, is located on a membrane (2). Preferably, as shown in FIG. 2, the membrane (2) is supported on a highly porous rigid support (14) to prevent flexing of the membrane due to pressure.

A liquid is selected that spontaneously fills the pores of the sample and the membrane. The sample and membrane pores (4) are filled with the liquid when the testing begins.

The fluid is preferably any fluid which effectively wets the sample (1), and preferably has low air diffusivity. A fluid with low air diffusivity is preferred because fluids with less air diffusivity do not produce bubbles which cause inaccuracies in measured volume of displaced fluid.

Air at pressures below the bubble point pressure of the membrane dissolve in the liquid in the pores of the membrane, diffuse through the liquid, and form bubbles in the liquid. The air bubbles displace liquid and the volume of displaced liquid increases although there is no displacement of liquid from pores of the sample. This error can be considerable in case of water in which the air solubility and diffusivity is high.

Examples of the fluid to be used include, but are not limited to, fluorocarbon, silicone, or any wetting fluid which the user might use in his product. Preferably, the fluid has a small (near zero) contact angle, low surface tension, low air solubility, low air diffusion and high viscosity.

Fluorocarbon and silicone liquids have low surface tension and the contact angle is zero for many materials. The low surface tension enables smaller pores to be measurable. Unchanging surface tension gives more accurate data. Zero constant contact angle gives more accurate and less uncertain results. Air solubility and diffusion in fluorocarbon and silicone liquids is very low. Fluorocarbon and silicone liquids have much less vapor pressure than water. Therefore, errors due to loss of liquid from pores is minimized.

The size of the pores (4) in the sample (1) may vary, depending on the nature of the sample. The membrane (2) needs to be chosen such that the smallest pore of interest in the sample is larger than the largest pore (5) in the membrane (2). Therefore, the membrane (2) preferably has a very small pore size to accommodate many different samples (1). An example of a membrane which has been used is Poretics polycarbonate membrane, catalog No. 13705, from Osmonics, Inc, of Minnetonka, Minn. Although the pores (5) in the membrane (2) are smaller than those in the sample (1), the pores (5) in the membrane (2) are preferably more numerous than the pores (4) in the sample (1), so that the permeability of the sample/membrane combination is determined by that of the sample rather than the membrane.

The bubble point of a sample (1) is pressure at a point that can overcome the capillary action of the fluid within the pores (4). The size of the pores in a material determines the bubble point, or the pressure at which the liquid is extruded or forced out of the pores—the bubble point is inversely proportional to the size of the pores.

Since the sample (1) in the sample chamber (12) has a larger pore size than the membrane (2), the bubble point of the pores (4) in the sample (1) is lower than the bubble point of the pores (5) in the membrane (2). Therefore, when sufficient gas or air pressure (6) is applied to exceed the bubble point of the sample (1), the fluid is forced out of the relatively larger pores (4) in the sample (1), and passes through the relatively smaller pores (5) in the membrane (2). The amount of pressure (6) applied should be high enough to exceed the bubble point of the smallest of the sample pores (4) of interest, but below the bubble point of the membrane (2), so that eventually all of the fluid is forced out of the sample pores (4), but no fluid is forced out of the membrane pores (5).

A reservoir of fluid (3) is located below the membrane (2). The fluid in the reservoir (3) is the same type of fluid as the fluid used to wet the sample (1). The extruded fluid which passed from the pores of the sample through the pores of the membrane displaces the fluid in the fluid reservoir (3). Thus, the total amount of fluid displaced from the reservoir will represent the amount of fluid which was trapped in the pores of the sample.

A penetrometer (25)—a relatively thin tube having a small bore to facilitate measurement of small volume changes is connected to the reservoir (3).

Figure 3:
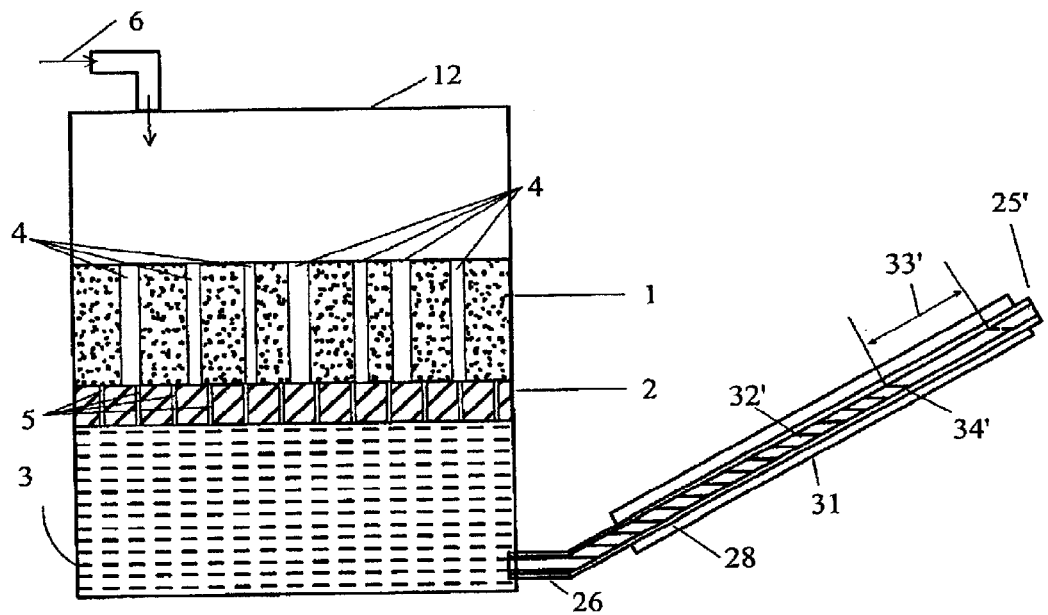
FIG. 3 shows an alternative embodiment of the device of the present invention.

In the embodiment of FIG. 2, the penetrometer (25) is made up of a horizontal portion (26) and a vertical portion (27), which meet at more or less a right angle. A column of fluid (32) enters the penetrometer (25). In the embodiment of FIG. 3, a slanted portion (28) replaces the vertical portion, to minimize the effects of the weight of the column of fluid (32') on the testing. In either embodiment, as fluid is forced through the membrane (2) into the reservoir (3), the level (34) or (34') in the penetrometer (25) or (25'), respectively, will rise.

The change (33) or (33') in the penetrometer fluid level (34) or (34') may be detected in a number of different ways. If the tube is made of transparent material, as noted above, the vertical (27) or slanted (28) portion of the penetrometer can be preferably calibrated by etched or painted markings (40), in any convenient scale, which would allow an operator to directly read the amount of fluid rise. Because the diameter of the penetrometer tube is known, the volume of fluid in the level rise can easily be calculated. If desired, the tube can be directly calibrated in volume, rather than units of length.

In a preferred embodiment, the level (34) is read by an electronic means. As shown in FIG. 2, a magnetic float (30) can be placed in the vertical tube (27). As the level (34) rises, the magnetic float (30) position can be sensed by a magnetic sensor (41), such as coils or Hall-effect sensors or other means known to the art, and the fluid rise (33) determined.

In the embodiment using a slanted penetrometer (25'), as shown in FIG. 3, a float is less practical. In this embodiment, the change (33') in fluid level (34') of the column of fluid (32') can be sensed by a capacitance sensor (31) external to the penetrometer tube (25'). The angled portion (28) is preferably drained periodically if too much fluid enters the penetrometer (25').

Before testing, the level (34) of (34') of fluid in the penetrometer (25) or (25') would be approximately the same as in the reservoir (3). That level would be the starting level for the test, if the test is started with a fully wetted sample. If the embodiment of the method which wets the sample in the chamber is used to wet the sample, the level in the penetrometer might change as excess fluid is forced through the sample (1), but at some point when the pressure has forced all of the excess fluid through the sample, but has not yet reached the bubble point of the largest pores, the level (34) or (34') will stop changing, and that will be taken as the starting level for the test.

Preferably, the apparatus is maintained at a constant low temperature during the testing, which will further limit bubble formation and lead to more accurate results.

The apparatus shown can also be used to measure permeability, either as a separate test or subsequent to the measurement of the pore volume. In such an application, the membrane (2) is either absent (if only permeability is to be tested) or has a sufficiently high number of pores (5) such that the permeability of the membrane is higher than the sample (1), and thus does not affect the total permeability of the sample/membrane combination.

In this embodiment, the apparatus measures permeability in the wetted sample (1) by starting with a quantity of fluid over the sample (2). As the pressure (6) increases, preferably in small steps, the fluid flows through the sample. By measuring the rate of flow through the sample (1) and the applied pressure (6) over time, the permeability of the sample (1) can be determined.

Once the excess fluid has passed through the sample, the measurements of permeability are complete. If it is desired to measure pore volume in the same run, the liquid level in the penetrometer can be measured as a starting point (it is possible that the penetrometer might need to be drained or disconnected during or after the flow measurement) and the method of the invention can proceed.

A flowchart of one method for measuring pore volume using the apparatus described above is shown in FIG. 4A. First, the sample is wet in step (100), preferably by adding a fluid which has low air diffusivity.

Once the sample is wet, it is placed on the membrane (2) in step (110). Alternatively, the sample could be placed on the membrane (step (110)) and then wet (step (100)) by putting the fluid on top of the sample (1) and membrane (2).

As previously mentioned, the pores (5) in the membrane (2) have a smaller pore size than any of the pores (4) in the sample (1).

The pressure is increased in a controlled manner, preferably in small steps of a few tenths of a psi, in step (120). Once the pressure exceeds the bubble point pressure, the fluid in the pores (4) begins to be pushed out of the largest pores (4) in the sample (1).

The extruded fluid enters the reservoir of fluid (3), displacing fluid already in the reservoir (3). This fluid enters the penetrometer (25) or (25').

The pressure (6) is continually increased, preferably in small steps, until the fluid in the penetrometer (25) or (25') reaches equilibrium. Equilibrium is reached when all of the fluid has been removed from of the pores (4) in the sample (1), and the fluid level is no longer increasing.

Once the fluid in the penetrometer (25) or (25') reaches equilibrium, the fluid level change in the penetrometer is measured in step (130). If penetrometer (25) is used, this step is preferably accomplished by sight or by using a magnetic float (30) in the penetrometer (25). If penetrometer (25') is used, a capacitance meter (31) preferably measures the fluid level change. The pore volume is then calculated using the fluid level measurement by techniques well known in the art.

Figure 4A:
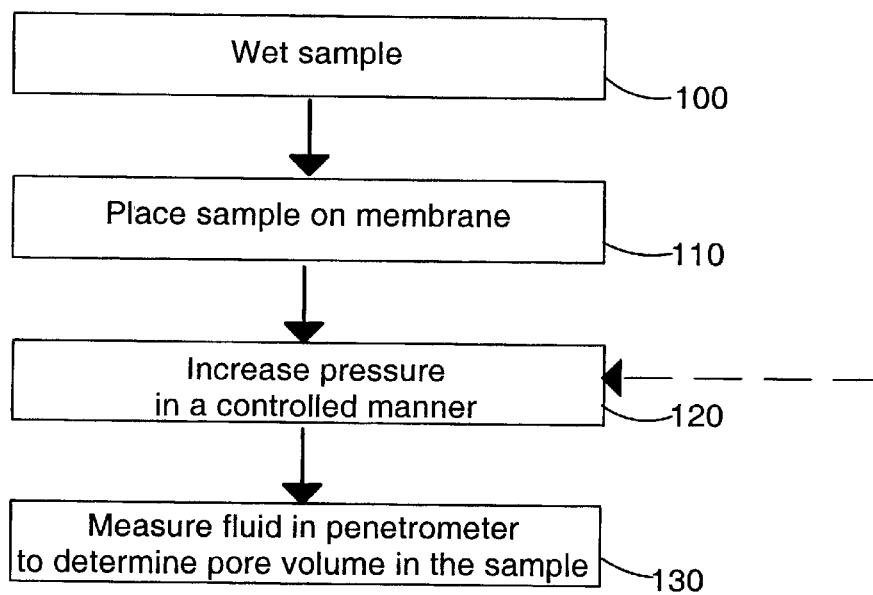
FIG. 4A shows a flowchart of one method of the present invention.
Figure 4B:
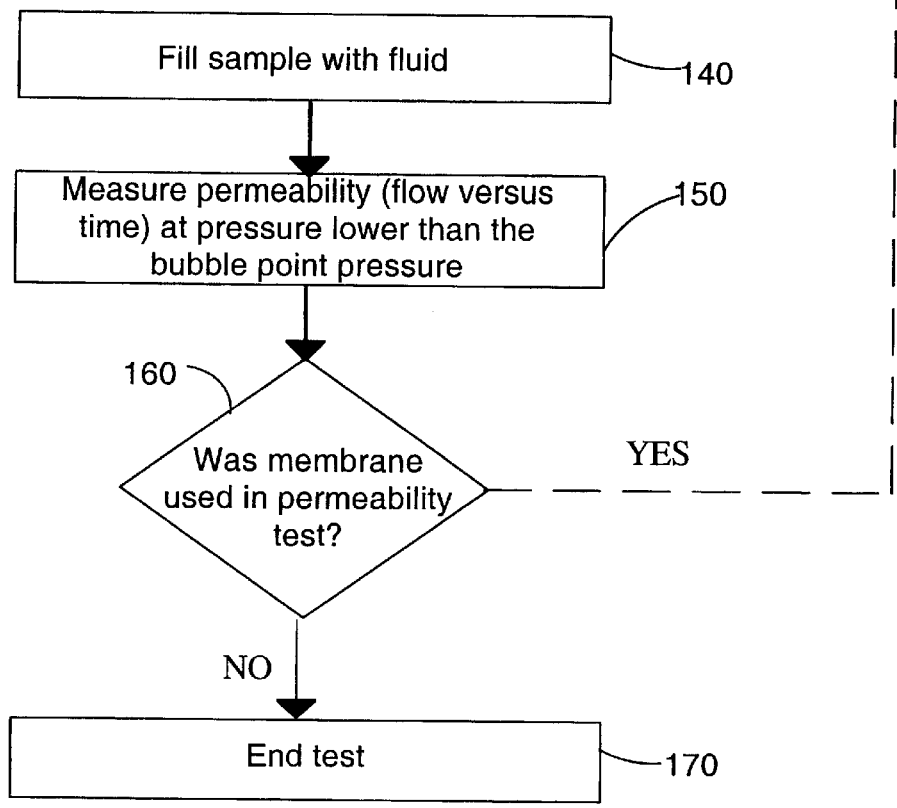
FIG. 4B shows a flowchart of an alternative method of the present invention.

A flowchart of an alternative method of the invention is shown in FIG. 4B. This method measures the permeability of the sample using the apparatus described above. The apparatus either has no membrane (2) or has a membrane (2) with a much higher permeability than that of the sample (1). The membrane (2) permeability must not affect the permeability measurements of the sample (1).

The sample (1) is filled with fluid in step (140). Permeability is measured in step (150). This is accomplished by measuring flow versus time.

If a user would like to also measure pore volume, steps (120) through (130) from FIG. 4A can be performed to measure pore volume in the sample (1). This combined method can only be used if a membrane was present during the permeability test. Therefore, in step (160) one asks whether or not a membrane was included in the apparatus during steps (140) and (150). If no, the method ends in step (170). If yes, the user may optionally perform steps (120) and (130) to determine the pore volume of the sample (1).

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of evaluating the porosity characteristics of a sample of material having a plurality of pores using a porosimeter comprising a pressurizable sample chamber for holding the sample, a membrane located at a bottom of the sample chamber and having a plurality of pores, wherein the membrane pores have a size smaller than any of the sample pores of interest, a reservoir of fluid located directly below the membrane, and a penetrometer coupled to the reservoir, wherein a level of fluid rises in the penetrometer when additional fluid enters the reservoir, comprising the steps of:
   a) wetting the sample and membrane with a fluid until the fluid has entered substantially all of the pores in the sample;
   b) applying a pressure in the sample chamber which is greater than a bubble point pressure of the sample, but less than a bubble point pressure of the membrane, until the fluid entering the penetrometer reaches an equilibrium; and
   c) measuring a fluid level change in the penetrometer between a fluid level before step (b) and a level after equilibrium.

2. The method of claim 1, wherein the fluid is a fluid with low air diffusivity.

3. The method of claim 1, wherein the fluid is selected from the group consisting of a fluorocarbon or silicone.

4. The method of claim 1, further comprising the step of calculating a pore volume of the sample using the fluid level change measured in step (c).

5. The method of claim 1, wherein the porosity characteristic being evaluated is the pore volume of the sample.

6. A method of evaluating the porosity characteristics of a sample of material having a plurality of pores using a porosimeter comprising a pressurizable sample chamber for holding the sample, a membrane located at a bottom of the sample chamber and having a plurality of pores, wherein the membrane pores have a size smaller than any of the sample pores of interest, a reservoir of fluid located directly below the membrane, and a penetrometer coupled to the reservoir, wherein a level of fluid rises in the penetrometer when additional fluid enters the reservoir, comprising the steps of:
   a) placing the sample in the sample chamber, on the membrane;
   b) wetting the sample and membrane with a fluid until the fluid has entered substantially all of the pores in the sample and membrane;
   c) adding a quantity of additional fluid above the sample in the sample chamber; and
   d) measuring flow rate of the fluid and applied pressure over time.

7. The method of claim 6, further comprising the step of calculating a permeability of the sample using the flow rate and pressure versus time measurements in step (d).

8. The method of claim 7, further comprising, after step (d), the steps of:
   e) applying a pressure in the sample chamber which is greater than a bubble point pressure of the sample, but less than a bubble point pressure of the membrane, until the fluid entering the penetrometer reaches an equilibrium; and
   f) measuring a fluid level change in the penetrometer between a fluid level before step (e) and a level after equilibrium.

9. The method of claim 8, further comprising the step of calculating a pore volume of the sample using the fluid level change measured in step (f).

10. The method of claim 6, wherein the fluid is a fluid with low air diffusivity.

11. The method of claim 6, wherein the fluid is selected from the group consisting of a fluorocarbon or silicone.

12. The method of claim 6, wherein the porosity characteristic being evaluated is the permeability of the sample.

13. A porosimeter for evaluating the porosity characteristics of a sample of material having a plurality of pores comprising:
   a) a pressurizable sample chamber for holding the sample,
   b) a membrane located at a bottom of the sample chamber and having a plurality of pores, wherein the membrane pores have a size smaller than any of the sample pores of interest,
   c) a reservoir for fluid located directly below the membrane; and
   d) a penetrometer coupled to the reservoir, such that if the reservoir is full of liquid, a level of fluid rises in the penetrometer when additional fluid enters the reservoir through the membrane.

14. The porosimeter of claim 13, further comprising a fluid having low air diffusivity.

15. The porosimeter of claim 14, wherein the fluid is selected from the group consisting of a fluorocarbon or silicone.

16. The porosimeter of claim 13, wherein the porosity characteristic being evaluated is the pore volume of the sample.

17. The porosimeter of claim 13, wherein the membrane has a higher permeability than the sample.

18. The porosimeter of claim 13, wherein the penetrometer comprises a tube.

19. The porosimeter of claim 18, wherein the penetrometer comprises a horizontal portion connected to the reservoir and a substantially vertical portion.

20. The porosimeter of claim 19, in which at least the vertical portion of the penetrometer is transparent and has a plurality of calibrations, such that the fluid level in the penetrometer can be measured by comparison to the calibrations.

21. The porosimeter of claim 19, further comprising a magnetic float in the penetrometer and a magnetic sensor adjacent to the penetrometer, such that the magnetic sensor measures a fluid level change in the penetrometer.

22. The porosimeter of claim 18, wherein the tube comprises a horizontal portion connected to the reservoir and an angled portion, wherein the angled portion meets the horizontal portion at an angle substantially less than ninety degrees.

23. The porosimeter of claim 22, further comprising a capacitance meter adjacent to the angled portion of the penetrometer, wherein the capacitance meter measures a fluid level change in the penetrometer.

* * * * *